United States Patent [19]

Shannon et al.

[11] Patent Number: 4,767,877
[45] Date of Patent: Aug. 30, 1988

[54] NITROGEN-CONTAINING BISPHENOL COMPOSITIONS

[75] Inventors: Thomas G. Shannon, Schenectady; Daniel J. Brunelle, Scotia, both of N.Y.

[73] Assignee: General Electric Company, Schenectady, N.Y.

[21] Appl. No.: 890,054

[22] Filed: Jul. 28, 1986

[51] Int. Cl.[4] ........................................ C07C 125/04
[52] U.S. Cl. .................................... 558/281; 544/338; 544/388; 558/266; 558/267; 560/22; 560/27; 564/156
[58] Field of Search .................... 564/156; 558/281

[56] References Cited

U.S. PATENT DOCUMENTS 3,903,160  9/1975  Dexter et al. .................. 564/156
4,564,705  1/1986  Frazer et al. ................... 564/156

OTHER PUBLICATIONS

Foldi et al., *J. Poly. Sci.*, 56, 1-9 (1962).

*Primary Examiner*—Glennon H. Hollrah
*Assistant Examiner*—James H. Turnipseed
*Attorney, Agent, or Firm*—William H. Pittman; James C. Davis, Jr.; James Magee, Jr.

[57] ABSTRACT

Bisamide and bisurethane bisphenols and bishaloformates are prepared by the reaction of amines with dicarboxylic acid halides or bisphenol bishaloformates. They are useful as intermediates for the preparation of cyclic heterocarbonates, which may in turn be converted to linear copolycarbonates.

14 Claims, No Drawings

NITROGEN-CONTAINING BISPHENOL COMPOSITIONS

This invention relates to bisphenol compositions useful in the preparation of cyclic heterocarbonates.

Cyclic heterocarbonates, disclosed and claimed in copending, commonly owned application Ser. No. 890,053, filed July 28, 1986, now U.S. Pat. No. 4,696,998 are valuable intermediates for the preparation of copolycarbonates. Such preparation may be achieved during extrusion or molding operations, or the copolycarbonates can be combined with fillers to form prepregs convertible to thermoplastic composites. The present invention provides novel nitrogen-containing bisphenols and bischloroformates useful as intermediates for the preparation of cyclic heterocarbonates.

In its broadest sense, the invention includes compositions comprising nitrogen-containing bisphenolic compounds of the formula

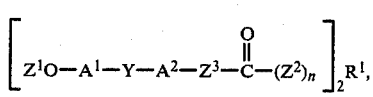  (I)

wherein:
each of $A^1$ and $A^2$ is a monocyclic divalent aromatic radical;
Y is a single bond or a bridging radical in which one or two atoms separate $A^1$ from $A^2$;
$Z^1$ is hydrogen or

n is 0 or 1;
$Z^2$ is oxygen or $NR^2$;
$Z^3$ is $NR^3$ if $Z^2$ is oxygen or n is 0, and is oxygen if n is 1 and $Z^2$ is $NR^2$;
$R^1$ is a divalent hydrocarbon radical and $R^2$ is hydrogen or a monovalent hydrocarbon radical, or $R^1$ and both $R^2$'s taken together are each an alkylene radical;
$R^3$ is hydrogen or a $C_{1-4}$ primary or secondary alkyl radical; and
X is chlorine or bromine.

As will be apparent from formula I, the compositions of this invention include bisphenols and bishaloformates derived therefrom. The preferred bishaloformates are the bischloroformates, wherein X is chlorine.

In formula I, the $A^1$ and $A^2$ values may be unsubstituted phenylene or substituted derivatives thereof, illustrative substituents (one or more) being alkyl, alkenyl (e.g., crosslinkable-graftable moieties such as vinyl and allyl), halo (especially chloro and/or bromo), nitro, alkoxy and the like. Unsubstituted phenylene radicals are preferred. Both $A^1$ and $A^2$ are preferably p-phenylene, although both may be o- or m-phenylene or one o- or m-phenylene and the other p-phenylene.

The Y value is a single bond or a bridging radical in which one or two atoms, preferably one, separate $A^1$ from $A^2$. It is most often a hydrocarbon radical and particularly a saturated radical such as methylene, cyclohexylmethylene, 2-[2.2.1]-bicycloheptylmethylene, ethylene, isopropylidene, neopentylidene, cyclohexylidene, cyclopentadecylidene, cyclododecylidene or adamantylidene, especially a gemalkylene (alkylidene) radical. Also included, however, are unsaturated radicals and radicals which contain atoms other than carbon and hydrogen; for example, 2,2-dichloroethylidene, carbonyl, oxy, sulfide, sulfoxy and sulfone.

The $A^1$, $A^2$ and Y radicals may be considered as being derived from bisphenols of the formula HO—$A^1$—Y—$A^2$—OH. The following bisphenols are illustrative:
Bis(4-hydroxyphenyl)methane
Bis(4-hydroxyphenyl)diphenylmethane
Bis(4-hydroxyphenyl)-1-naphthylmethane
1,1-Bis(4-hydroxyphenyl)ethane
1,2-Bis(4-hydroxyphenyl)ethane
1,1-Bis(4-hydroxyphenyl)-1-phenylethane
2,2-Bis(4-hydroxyphenyl)propane ("bisphenol A")
2-(4-Hydroxyphenyl)-2-(3-hydroxyphenyl)propane
2,2-Bis(4-hydroxyphenyl)butane
1,1-Bis(4-hydroxyphenyl)isobutane
1,1-Bis(4-hydroxyphenyl)cyclohexane
1,1-Bis(4-hydroxyphenyl)cyclododecane
Trans-2,3-bis(4-hydroxyphenyl)-2-butene
2,2-Bis(4-hydroxyphenyl)adamantane
α,α'-Bis(4-hydroxyphenyl)toluene
Bis(4-hydroxyphenyl)acetonitrile
2,2-Bis(3-methyl-4-hydroxyphenyl)propane
2,2-Bis(3-ethyl-4-hydroxyphenyl)propane
2,2-Bis(3-n-propyl-4-hydroxyphenyl)propane
2,2-Bis(3-isopropyl-4-hydroxyphenyl)propane
2,2-Bis(3-sec-butyl-4-hydroxyphenyl)propane
2,2-Bis(3-t-butyl-4-hydroxyphenyl)propane
2,2-Bis(3-cyclohexyl-4-hydroxyphenyl)propane
2,2-Bis(3-allyl-4-hydroxyphenyl)propane
2,2-Bis(3-methoxy-4-hydroxyphenyl)propane
2,2-Bis(3,5-dimethyl-4-hydroxyphenyl)propane
2,2-Bis(2,3,5,6-tetramethyl-4-hydroxyphenyl)propane
2,2-Bis(3-5-dichloro-4-hydroxyphenyl)propane
2,2-Bis(3,5-dibromo-4-hydroxyphenyl)propane
2,2-Bis(2,6-dibromo-3,5-dimethyl-4-hydroxyphenyl)propane
α,α-Bis(4-hydroxyphenyl)toluene
α,α,α', α'-Tetramethyl-α,α'-bis(4-hydroxyphenyl)-p-xylene
2,2-Bis(4-hydroxyphenyl)hexafluoropropane
1,1-Dichloro-2,2-bis(4-hydroxyphenyl)ethylene
1,1-Dibromo-2,2-bis(4-hydroxyphenyl)ethylene
1,1-Dichloro-2,2-bis(5-phenoxy-4-hydroxyphenyl)ethylene
4,4'-Dihydroxybenzophenone
3,3-Bis(4-hydroxyphenyl)-2-butanone
1,6-Bis(4-hydroxyphenyl)-1,6-hexanedione
Ethylene glycol bis(4-hydroxyphenyl) ether
Bis(4-hydroxyphenyl) ether
Bis(4-hydroxyphenyl) sulfide
Bis(4-hydroxyphenyl) sulfoxide
Bis(4-hydroxyphenyl) sulfone
Bis(3,5-dimethyl-4-hydroxyphenyl) sulfone.

Preferably, $A^1$ and $A^2$ are each p-phenylene and Y is isopropylidene.

The compositions of this invention include bisamides, in which n is 0, and bisurethanes, in which n is 1. Thus, when n is 1, the $Z^2$ value may be oxygen or amino nitrogen, and the $Z^3$ value is amino nitrogen when $Z^2$ is oxygen and vice versa. The third valence of each amino nitrogen atom may be satisfied by hydrogen or a hydrocarbon radical as previously defined; it is usually hydrogen when n is 0 and hydrogen, alkyl, aryl or alkylene (as specified hereinafter) when n is 1.

The $R^1$ value may be a divalent aliphatic, alicyclic or aromatic hydrocarbon radical, typically containing about 2–20 carbon atoms. It is most often a $C_{2-6}$ alkylene radical; a phenylene radical, especially m- or p-phenylene; or a 4,4'-biphenylene or $C_{13-20}$ bis(4-phenylene)alkane radical.

When $R^1$ is alkylene, both $R^2$ values taken together may also be alkylene, usually identical to $R^1$. The preferred compounds of this type are those in which $R^1$ and both $R^2$'s taken together are each ethylene. The $R^2$ value may also be hydrogen or a monovalent aliphatic, alicyclic or aromatic hydrocarbon radical. In that case, it is usually $C_{1-4}$ primary or secondary alkyl, especially methyl, or phenyl. The same types of alkyl radicals are preferred for $R^3$.

The nitrogen-containing bisphenolic compounds of this invention may be prepared by conventional reactions between amines and dicarboxylic acid halides or bisphenol bishaloformates. Thus, bisamide bisphenols of formula I wherein n is 0 and $Z^3$ is $NR^3$ may be prepared, for example, by the reaction of a dicarboxylic acid chloride of the formula $R^1(COCl)_2$ with an aminophenol of the formula HO—$A^1$—Y—$A^2$—$NHR^3$.

Similarly, bisurethane bisphenols and the corresponding bischloroformates of formula I may be prepared by the reaction of bisphenol bischloroformates with diamines or hydroxyaromatic amines. For example, the reaction of bischloroformates of the formula ClCOO—$A^1$—Y—$A^2$—OCOCl with a diamine of the formula $R^1(NHR^2)_2$ produces bisurethane bisphenols in which $Z^2$ is $NR^2$ and $Z^3$ is oxygen. On the other hand, the reaction of a bisphenol bischloroformate of the formula $R^1(OCOCl)_2$ with a hydroxy amine of the formula HO—$A^1$—Y—$A^2$—$NHR^3$ produces a bisurethane bisphenol in which $Z^2$ is oxygen and $Z^3$ is $NR^3$.

These reactions may be conducted under conventional conditions, using appropriate mole ratios of reagents and conventional reaction media. It is frequently advantageous to employ at least one hydrogen halide scavenger, typically a tertiary amine or an alkali metal carbonate or bicarbonate.

The preparation of the nitrogen-containing bisphenolic compounds of this invention is illustrated by the following examples.

EXAMPLE 1

A mixture of 50 mmol. of 2-(4-hydroxyphenyl)-2-(4-methylaminophenyl)propane, 50 mmol. of sodium bicarbonate, 500 ml. of water and 50 ml. of methylene chloride was mixed at high speed in a blender as a solution of 25 mmol. of isophthaloyl chloride in 25 ml. of methylene chloride was added over 5 minutes. Blending was continued for 10 minutes, yielding a heterogeneous mixture which was extracted with ethyl acetate. Upon vacuum stripping, the desired bisamide bisphenol was obtained; it was shown by infrared and proton nuclear magnetic resonance spectroscopy to have the formula

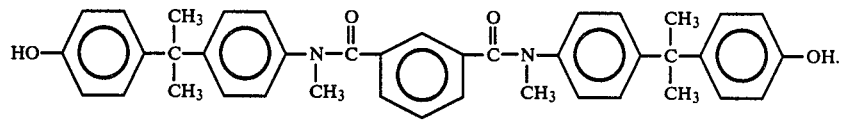

By a similar procedure, an isomeric bisamide bisphenol was prepared from terephthaloyl chloride.

EXAMPLE 2

To 50 ml. of a 1M solution in methylene chloride of bisphenol A bischloroformate (50 mmol.) maintained at 0° C., was added slowly, with stirring, a solution of 1.194 grams (10 mmol.) of piperazine hexahydrate in 10 ml. of a mixture of equal volumes of tetrahydrofuran and water. Stirring was continued for 15 minutes to produce a solution comprising a bisurethane bischloroformate having the formula

EXAMPLE 3

Triethylamine, 2.2 grams (20 mmol.), was slowly added at 0° C., with stirring, to a solution of 10.5 grams (30 mmol.) of bisphenol A bischloroformate in 50 ml. of methylene chloride. There was then added over 15 minutes a solution of 2.5 grams of 85% pure N,N'-diphenylethylenediamine (10 mmol.) in 20 ml. of methylene chloride. The mixture was stirred for 10 minutes, washed with dilute aqueous hydrochloric acid, dried and vacuum stripped, yielding a tan solid. A sample of the product was dissolved in methylene chloride, precipitated with hexane, redissolved in methylene chloride and vacuum stripped to yield a light brown crystalline solid which was shown by proton nuclear magnetic resonance spectroscopy to be the desired bisurethane bischloroformate having the formula

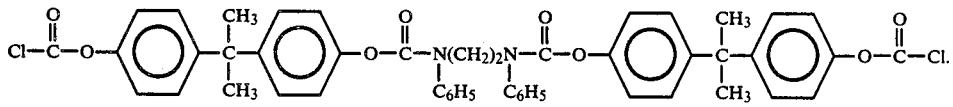

EXMAPLE 4

A solution of 51 mg. (0.25 mmol.) of bis(4-aminophenyl)methane in 2 ml. of methylene chloride was added at 0° C. over 15 minutes, with stirring, to a methylene chloride solution of 1.56 grams (3 mmol.) of bisphenol A bischloroformate and 100 mg. (1 mmol.) of triethylamine. There was obtained a methylene chloride solution of a bisurethane bischloroformate having the formula

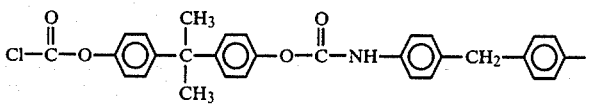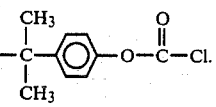

EXAMPLE 5

A solution of 10 mmol. of 2-(4-hydroxyphenyl)-2-(4-methylaminophenyl)propane and 5 mmol. of bisphenol A bischloroformate in 50 ml. of methylene chloride was placed in a small blender and agitated for 10 minutes, during which time a precipitate formed. There was then added a solution of 15 mmol. of sodium carbonate in 50 ml. of water, and the mixture was blended for an additional 1½ hours. The organic layer was separated, dried with phase separation paper and stripped in a rotary evaporator to yield a fluffy white solid. The solid was washed twice with hexane, dissolved in a small amount of methylene chloride and precipitated slowly by the addition of ethyl ether. The precipitate was filtered, washed twice with ether and dried to yield the desired bisurethane bisphenol having the formula

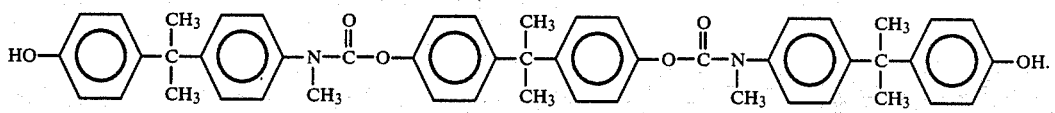

EXAMPLE 6

The procedure of Example 5 was repeated, substituting hydroquinone bischloroformate on an equimolar basis for the bisphenol A bischloroformate. A similar product was obtained; it has the formula

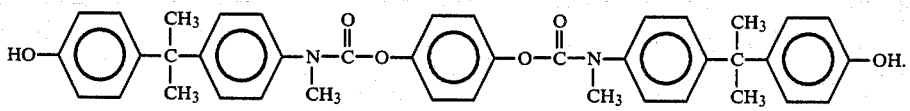

EXAMPLE 7

The procedure of Example 5 was repeated, substituting resorcinol bischloroformate on an equimolar basis for the bisphenol A bischloroformate. A bisurethane which was soluble in ethyl ether was obtained; it had the formula

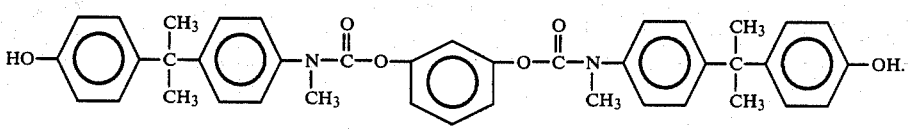

As indicated hereinabove, the nitrogen-containing bisphenolic compounds of this invention are useful for the preparation of cyclic heterocarbonates, as disclosed and claimed in the aforementioned U.S. Pat. No. 4,696,998. Particularly useful in this regard are the bishaloformates. The bisphenols are of interest principally as intermediates for the preparation of said bishaloformates.

The cyclic heterocarbonates may be prepared by reacting (A) a composition comprising at least one bishaloformate of this invention, or a mixture thereof with at least one bisphenol, with (B) at least one oleophilic, aliphatic or heterocyclic tertiary amine, and (C) an aqueous alkali or alkaline earth metal hydroxide or carbonate solution;

in (D) a substantially non-polar organic liquid which forms a two-phase system with water. The details of preparation are similar to those for preparing cyclic polycarbonate oligomers as described in European patent application No. 162,379 and in copending, commonly owned application Ser. No. 871,641, filed June 6, 1986, now U.S. Pat. No. 4,605,731 the disclosures of which are incorporated by reference herein.

Reagent A may be a mixture of bisphenols and bischloroformates, usually containing up to about 5 moles of bischloroformate per mole of bisphenol, or it may contain only bischloroformates. The latter situation is usually preferred.

The tertiary amines useful as reagent B ("tertiary" in this context denoting the absence of N—H bonds) generally comprise those which are oleophilic (i.e., which are soluble in and highly active in organic media, especially those used in the oligomer preparation method of this invention), and more particularly those which are useful for the formation of polycarbonates. Reference is made, for example, to the tertiary amines disclosed in U.S. Pat. Nos. 4,217,438 and 4,368,315, the disclosures of which are incorporated by reference herein. They include aliphatic amines such as triethylamine, tri-n-propylamine, diethyl-n-propylamine and tri-n-butylamine and highly nucleophilic heterocyclic amines such as 4-dimethylaminopyridine (which, for the purposes of this invention, contains only one active amine group). The preferred amines are those which dissolve preferentially in the organic phase of the reaction system; that is, for which the organic-aqueous partition coefficient is greater than 1. This is true because intimate contact between the amine and reagent A is essential for the formation of the cyclic heterocarbonate. For the most part, such amines contain at least about 6 and preferably about 6-14 carbon atoms.

The amines most useful as reagent B are trialkylamines containing no branching on the carbon atoms in the 1- and 2-positions. Especially preferred are tri-n-alkylamines in which the alkyl groups contain up to about 4 carbon atoms. Triethylamine is most preferred by reason of its particular availability, low cost, and effectiveness.

Reagent C is an aqueous alkali or alkaline earth metal hydroxide or carbonate solution, such as lithium, sodium, potassium or calcium hydroxide or sodium or potassium carbonate. It is most often lithium, sodium or potassium hydroxide, with sodium hydroxide being preferred because of its availability and relatively low cost. The concentration of said solution is not critical; it is generally about 0.1-16M, preferably about 0.2-10M and most desirably no higher than about 5M.

The fourth essential component (component D) in the cyclic heterocarbonate preparation method is a substantially non-polar organic liquid which forms a two-phase system with water. The identity of the liquid is not critical, provided it possesses the stated properties. Illustrative liquids are aromatic hydrocarbons such as toluene and xylene; substituted aromatic hydrocarbons such as chlorobenzene, o-dichlorobenzene and nitrobenzene; chlorinated aliphatic hydrocarbons such as chloroform and methylene chloride; and mixtures of the foregoing with ethers such as tetrahydrofuran. Methylene chloride is generally preferred.

To prepare the cyclic heterocarbonate, the reagents and components are maintained in contact under conditions whereby reagent A is present in low concentration. Actual high dilution conditions, requiring a large proportion of component D, may be employed but are usually not preferred for cost and convenience reasons. Instead, simulated high dilution conditions known to those skilled in the art may be employed. For example, in one embodiment of the method reagent A or reagents A and B are added gradually to a mixture of the other materials. It is within the scope of this embodiment to incorporate reagent B in the mixture to which reagent A is added, or to add it gradually, either in admixture with reagent A or separately. Continuous or incremental addition of reagent B is frequently preferred.

Although addition of reagent A neat (i.e., without solvents) is within the scope of this embodiment, it is often preferably added as a solution in a portion of component D. The proportion of organic liquid used for this purpose is not critical; about 25-75% by weight, and especially about 40-60%, is often preferred.

The reaction temperature is generally in the range of about 0°-50° C. It is most often about 0°-40° C. and preferably 20°-40° C.

For maximization of the yield and purity of cyclic heterocarbonates, it is preferred to use up to about 0.7 mole and preferably about 0.1-0.6 mole of reagent A per liter of component D in the reaction system, including any liquid used to dissolve reagent A. (It should be noted that this is not a molar concentration in component D when reagent A is added gradually, since said reagent is consumed as it is added to the reaction system.) The preferred molar ratio of reagent B to reagent A is about 0.05-1.5:1 and most often about 0.1-1.0:1.

The molar ratio of reagent C to reagent A is usually about 1-5:1 and preferably about 1-3:1.

A highly preferred embodiment of the method for preparing the cyclic heterocarbonates comprises gradually adding reagent A and at least a portion of reagents B and C simultaneously to a substantially non-polar organic liquid (component D) or to a mixture of said liquid with water. A factor of some importance in this embodiment is the concentration of available reagent B, which should be maintained at a level as constant as possible during the entire addition period for reagent A. If all of reagent B is present in the reaction vessel into which reagent A is introduced, its concentration steadily decreases, principally by dilution. On the other hand, if reagent B is introduced continuously or in equal increments during introduction of reagent A, its available concentration is initially low and increases more or less steadily during the addition period. These fluctuations can result in a high and constantly varying proportion of high polymer (i.e., linear or cyclic polymer with a weight average molecular weight higher than about 30,000) in the product.

It has been found advantageous to introduce reagent B in one initial large portion, usually about 40-95% and preferably about 40-75% by weight of the total amount, followed by incremental or continuous addition of the balance thereof. By this procedure, the concentration of available reagent B is maintained at a fairly constant level in the organic phase during the entire addition period, and it is possible to minimize the proportion of high polymer in the product.

Under these conditions, it is usually advantageous for the reaction vessel to initially contain about 5-40% and preferably about 5-30% of total reagent C. The balance thereof is also introduced continuously or incrementally.

In general, cyclic heterocarbonates prepared under these conditions contain very low proportions of linear oligomers. In many instances no more than about 5% by weight, and frequently no detectable amount, of such linear oligomers are present. Many products of this invention also contain low percentages (frequently less than 20% and preferably no higher than about 10%) of polymers (linear or cyclic) having a weight average molecular weight greater than about 30,000. Such polymers are frequently identified hereinafter as "high polymer".

When necessary, linears, high polymer and other impurities may be removed by conventional operations such as combining the solution with a non-solvent for said impurities. Illustrative non-solvents include ketones such as acetone and methyl isobutyl ketone and esters such as methyl acetate and ethyl acetate. Acetone is a particularly preferred non-solvent.

The preparation of cyclic heterocarbonates from the bisphenolic compounds of this invention is illustrated by the following examples.

EXAMPLE 8

A mixture of 6.12 grams (10 mmol.) of the bisamide bisphenol of Example 1 and 50 ml. of methylene chloride was cooled to 0° C. and phosgene was passed in at 1 gram per minute for 3 minutes. A solution of 3 grams (20 mmol.) of diethylaniline in methylene chloride was then added slowly, with stirring, as the temperature was maintained at 0° C. The mixture was allowed to warm to room temperature over 15 minutes and stirred for one additional hour. Toluene, 50 ml., was then added with stirring and the mixture was sparged with nitrogen to remove excess phosgene and methylene chloride. The toluene solution was washed with dilute aqueous hydrochloric acid and water, yielding the crude bischloroformate.

A solution of the crude bischloroformate in 10 ml. of methylene chloride was added over 35 minutes, with stirring, to a refluxing mixture of 25 ml. of methylene chloride, 1 ml. of 5M aqueous sodium hydroxide solution and 0.1 ml. of triethylamine. There were simultaneously added in equal portions, at 7-minute intervals, 4 ml. of 5M aqueous sodium hydroxide solution and 0.11 ml. of triethylamine. When addition was complete, the organic and aqueous phases were separated and the aqueous phase was washed with a small portion of methylene chloride. The combined organic phases were washed three times with dilute aqueous hydrochloric acid and once with water, dried and evaporated to yield the desired cyclic bisamide carbonate oligomer mixture, melting in the range of 140°-160° C. It was shown by high pressure liquid-liquid chromatographic analysis to comprise 2.9% monomer, 43.2% dimer, 21.35% trimer, 9.42% tetramer and minor amounts of higher oligomers.

EXAMPLE 9

The bischloroformate solution of Example 2 was added over 30 minutes to a slowly stirred mixture of 200 ml. of methylene chloride, 50 ml. of 2.5M aqueous sodium hydroxide solution and 2.5 grams of triethylamine. When addition was complete, the product was worked up as described in Example 8. There was obtained the desired cyclic bisurethane carbonate product. It was shown by high pressure liquid-liquid chromatography, after removal of high polymer by precipitation with acetone, to comprise mixed cyclics and by field desorption mass spectrometry to contain substantial proportions of compounds of the formula

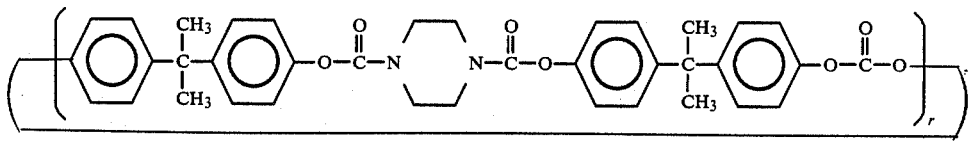

wherein r is 1 and 2.

EXMAPLE 10

The procedure of Example 9 was repeated, using a bischloroformate mixture corresponding to a 7:1 molar ratio of bisphenol A bischloroformate to bisurethane bischloroformate. A mixed cyclic polycarbonate product containing cyclic polyurethane carbonates was obtained.

EXMAPLE 11

A solution of 1 mmol. of the bisurethane bischloroformate in Example 3 in 10 ml. of methylene chloride was added over 30 minutes to a stirred mixture of 20 ml. of methylene chloride, 2 ml. of 1M aqueous sodium hydroxide and 40 mg. (0.4 mmol.) of triethylamine. After addition was complete, the sample was worked up as described in Example 8. High pressure liquid-liquid chromatographic analysis showed the existence of the desired cyclic bisurethane carbonate.

EXAMPLE 12

The bischloroformate solution of Example 4 was added over 25 minutes to a mixture of 10 ml. of methylene chloride, 2 ml. of 1M aqueous sodium hydroxide solution and 50 mg. of triethylamine. Upon workup as described in Example 8, the desired cyclic bisurethane-carbonate was obtained.

EXAMPLES 13-14

Following a procedure similar to that of Example 11, the products of Examples 5-6 were converted to bischloroformates and cyclized to yield the desired bisurethane carbonate oligomer mixtures.

EXAMPLE 15

The bisphenol of Example 7 was converted to bischloroformate and cyclized to a bisurethane carbonate oligomer mixture by the procedure of Example 8.

The cyclic heterocarbonates are in turn useful as intermediates for conversion to linear copolycarbonates. The method of preparation of such copolycarbonates comprises contacting at least one of the previously defined cyclic heterocarbonates with a polycarbonate formation catalyst at a temperature up to about 350° C.

The polycarbonate formation catalysts which can be used include various bases and Lewis acids. It is known that basic catalysts may be used to prepare polycarbonates by the interfacial method, as well as by transesterification and from cyclic oligomers. Reference is made to the aforementioned U.S. Pat. Nos. 3,155,683, 3,274,214, 4,217,438 and 4,368,315. Such catalysts may also be used to polymerize the cyclic oligomer mixtures. Examples thereof are lithium 2,2,2-trifluoroethoxide, n-butyllithium and tetramethylammonium hydroxide. Also useful are various weakly basic salts such as sodium benzoate and lithium stearate.

A particularly useful class of Lewis bases is disclosed in copending, commonly owned application Ser. No. 723,672, filed Apr. 16, 1985, now U.S. Pat. No. 4,605,731. It includes numerous tetraarylborate salts, including lithium tetraphenylborate, sodium tetraphenylborate, sodium bis(2,2'-biphenylene)borate, potassium tetraphenylborate, tetramethylammonium tetraphenylborate, tetra-n-butylammonium tetraphenylborate, tetramethylphosphonium tetraphenylborate, tetra-n-butylphosphonium tetraphenylborate and tetraphenylphosphonium tetraphenylborate. The preferred catalysts within this class are the tetra-n-alkylammonium and tetra-n-alkylphosphonium tetraphenylborates. Tetramethylammonium tetraphenylborate is particularly preferred because of its high activity, relatively low cost and ease of preparation from tetramethylammonium hydroxide and an alkali metal tetraphenylborate.

Lewis acids useful as polycarbonate formation catalysts include dioctyltin oxide, triethanolaminetitanium isopropoxide, tetra(2-ethylhexyl) titanate and polyvalent metal (especially titanium and aluminum) chelates such as bisisopropoxytitanium bisacetylacetonate (commercially available under the tradename "Tyzor AA") and the bisisopropoxyaluminum salt of ethyl acetoacetate. Among the preferred catalysts are lithium stearate and bisisopropoxytitanium bisacetylacetonate.

The copolycarbonate formation reaction is typically effected by merely contacting the cyclic heterocarbonate with the catalyst at temperatures up to 350° C., preferably about 200°-300° C., until polymerization has proceeded to the extent desired. Although the use of a solvent is within the scope of the invention, it is generally not preferred. In general, the amount of catalyst used is about 0.001–1.0 mole percent based on carbonate structural units in the heterocarbonate.

The conditions of the polymerization reaction may be varied to produce resinous compositions of various molecular weights and molecular weight distributions (i.e., Mw/Mn ratios). Molecular weight can be controlled by varying the amount of catalyst, with a decrease in said amount generally resulting in an increase in molecular weight, or by employing known chain transfer or endcapping agents, of which diphenyl carbonate is an example, typically in amounts up to about 2.5 mole percent based on carbonate structural units in the heterocarbonate.

Among the processing operations which can be conducted simultaneously with polymerization are various extrusion and molding operations. Thus, the cyclic heterocarbonates may be combined with polycarbonate formation catalysts of the type described hereinabove and fed to an extruder which is maintained at polymerization temperature. The effluent from the extruder is then a polycarbonate in the desired sheet, rod or other form. The molecular weight of the product may be adjusted over a wide range by methods previously described.

Similarly, the cyclic heterocarbonates may be combined with polycarbonate formation catalysts and injection molded at polymerization temperatures. Said heterocarbonates also have flow properties adequate for rotational molding simultaneous with polymerization. These capabilities make it possible to employ the cyclic heterocarbonates of this invention in operations previously unavailable with respect to copolycarbonates.

The cyclic heterocarbonates are also advantageously combined with inert filler materials to produce prepreg compositions which may be polymerized to thermoplastic composites having excellent impact resistance, moisture resistance and ductility. The composites have a number of advantages over the somewhat more well known thermoset composites, such as the capability of being shaped after polymerization is completed.

The preparation of copolycarbonates from the cyclic heterocarbonates is illustrated by the following examples. All molecular weights are weight average and were determined by gel permeation chromatography relative to polystyrene.

EXMAPLE 16

To a solution of 508 mg. of the cyclic polyurethane carbonate of Example 9 (from which high polymer had been removed by precipitation with acetone) in 25 ml. of methylene chloride was added 0.79 mg. of tetramethylammonium tetraphenylborate. The solvent was removed by vacuum evaporation and the solid residue was dried for 4 hours in a vacuum oven at 80° C. It was then heated under nitrogen at 200° C. for 2 hours to yield the desired copolycarbonate having a molecular weight of 46,000.

EXAMPLES 17–19

Following the procedure of Example 16, various cyclic heterocarbonates were combined with 0.25 mole percent (based on carbonate structural units) of tetra-n-butylammonium tetraphenylborate and were polymerized by heating under nitrogen for 20–25 minutes at 275° C. The identities of the reactants and the molecular weights and glass transition temperatures of the products are given in the following table.

| Example | Cyclic heterocarbonate | Mw | Tg, °C. |
|---|---|---|---|
| 17 | Ex. 8 | — | 154 |
| 18 | Ex. 10 | 53,500 | 148.1 |
| 19 | Ex. 13 | 61,000 | 153.4 |

*3:1 ratio of ester to carbonate groups.

What is claimed is:

1. A nitrogen-containing bisphenolic compound having the formula

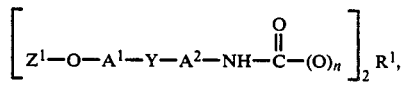

wherein:
each of $A^1$ and $A^2$ is a divalent unsubstituted or alkyl-, alkenyl-, halo-, nitro- or alkoxy-substituted phenylene radical;
Y is a single bond, a hydrocarbon radical in which one or two atoms separate $A^1$ from $A^2$, 2,2-dichloroethylidene, carbonyl, oxy, sulfide, sulfoxy or sulfone;
$Z^1$ is hydrogen or

$R^1$ is a divalent hydrocarbon radical;
X is chlorine or bromine; and
n is 0 or 1.

2. A compound according to claim 1 wherein $A^1$ and $A^2$ are each p-phenylene.

3. A compound according to claim 2 wherein Y is isopropylidene.

4. A compound according to claim 3 wherein $R^1$ is $C_{2-6}$ alkylene, m- or p-phenylene, 4,4'-biphenylene or $C_{13-20}$ bis(4-phenylene)alkane.

5. A compound according to claim 4 wherein n is O.

6. A compound acording to claim 5 wherein $R^1$ is m- or p-phenylene.

7. A compound according to claim 6 wherein $Z^1$ is hydrogen or

8. A compound according to claim 7 which has the formula

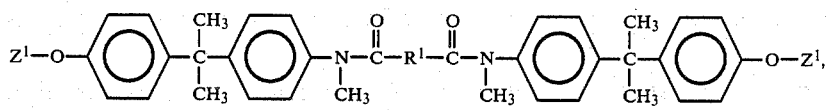

wherein $R^1$ is m- or p-phenylene.

9. A compound according to claim 4 wherein n is 1.

10. A compound according to claim 9 wherein $R^1$ is m- or p-phenylene, 4,4'-biphenylene or $C_{13-20}$ bis(4-phenylene)alkane.

11. A compound according to claim 10 wherein $Z^1$ is hydrogen or

12. A compound according to claim 11 which has the formula

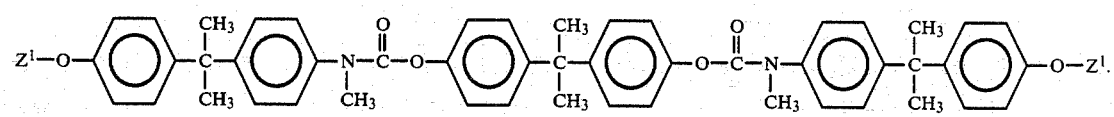

13. A compound according to claim 11 which has the formula

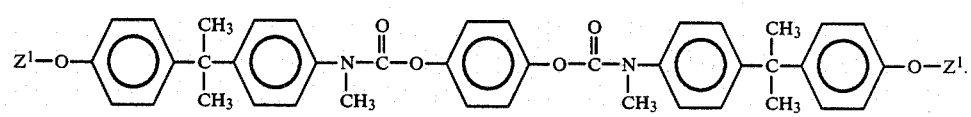

14. A compound according to claim 11 which has the formula

* * * * *